(12) United States Patent
Swanson (10) Patent No.: US 12,140,510 B2
(45) Date of Patent: Nov. 12, 2024

(54) LOW FLOW-THROUGH VIAL

(71) Applicant: BL TECHNOLOGIES, INC., Minnetonka, MN (US)

(72) Inventor: Lukas Swanson, Victor, MT (US)

(73) Assignee: BL TECHNOLOGIES, INC., Minnetonka, MN (US)

( * ) Notice: Subject to any disclaimer, the term of this patent is extended or adjusted under 35 U.S.C. 154(b) by 387 days.

(21) Appl. No.: 17/620,340

(22) PCT Filed: Jun. 26, 2019

(86) PCT No.: PCT/US2019/039172
§ 371 (c)(1),
(2) Date: Dec. 17, 2021

(87) PCT Pub. No.: WO2020/263238
PCT Pub. Date: Dec. 30, 2020

(65) Prior Publication Data
US 2022/0316995 A1   Oct. 6, 2022

(51) Int. Cl.
*G01N 1/20*   (2006.01)
*G01N 33/18*   (2006.01)

(52) U.S. Cl.
CPC ....... *G01N 1/2035* (2013.01); *G01N 33/1846* (2013.01); *G01N 2001/2085* (2013.01)

(58) Field of Classification Search
CPC .............. G01N 1/2035; G01N 33/1846; G01N 2001/2085
See application file for complete search history.

(56) References Cited

U.S. PATENT DOCUMENTS 5,132,094 A   7/1992   Godec et al.
5,902,751 A   5/1999   Godec et al.
(Continued)

FOREIGN PATENT DOCUMENTS

CN   104884928 A   9/2015
DE   29520701   3/1996
(Continued)

OTHER PUBLICATIONS

Suez, "Sievers M9 TOC Analyzers" manual, Aug. 2018, Published by Siever Instruments (Year: 2018).*
(Continued)

*Primary Examiner* — Peter J Macchiarolo
*Assistant Examiner* — John M Royston
(74) *Attorney, Agent, or Firm* — Meunier Carlin & Curfman LLC (57) ABSTRACT

Various implementations include a device for analyzing total organic carbon (TOC) within a fluid. The device includes a primary container, an input conduit, and an output conduit. The primary container is hollow and has a primary side wall and a primary end wall. The primary side wall has an inner surface defining a primary cavity and an outer surface opposite and spaced apart from the inner surface. The primary end wall includes a septum that is resiliently penetrable by an analyzer needle of a grab analysis port of a TOC analyzer. The input conduit has an input lumen. The input conduit extends through the primary container such that the input lumen is in fluid communication with the primary cavity. The output conduit has an output lumen.

16 Claims, 4 Drawing Sheets

(56) References Cited

U.S. PATENT DOCUMENTS

| | | | |
|---|---|---|---|
| 8,003,048 B2 | 8/2011 | Clay et al. | |
| 9,074,967 B2 | 7/2015 | Clay | |
| 2013/0045540 A1 | 2/2013 | Collier et al. | |
| 2013/0243651 A1* | 9/2013 | Oprea | B01L 3/563 422/63 |
| 2014/0174207 A1 | 6/2014 | Clay | |
| 2015/0075302 A1* | 3/2015 | Jenkins | G01N 1/20 73/863.23 |
| 2015/0297874 A1* | 10/2015 | East | A61M 39/225 604/9 |

FOREIGN PATENT DOCUMENTS

| | | |
|---|---|---|
| DE | 202004015941 | 12/2004 |
| JP | 19750172664 U | 12/1975 |
| JP | 5284290 S | 6/1977 |
| JP | 656163452 | 12/1981 |
| JP | 2009510472 A | 3/2009 |
| JP | 2013-044750 A | 3/2013 |
| JP | 2016502101 A | 7/2015 |
| WO | 2014099296 A1 | 6/2014 |

OTHER PUBLICATIONS

Notice of Reasons for Refusal for corresponding Japanese Patent Application No. 2021-577000 dated Jul. 11, 2023.
International Search Report and Written Opinion dated Mar. 24, 2020, from International Application No. PCT/US2019/039172, 17 pages.
Office Action issued for Chinese Application No. 201980097839.2, dated Sep. 25, 2023.
Office Action issued for Japanese Application No. 2021-577000, dated Feb. 14, 2023.
Office Action, dated Oct. 6, 2022, received in connection with corresponding EP Patent Application No. 19740170.6.
Office Action in connection with EP Application No. 19740170.6, dated Jul. 26, 2024.

* cited by examiner

LOW FLOW-THROUGH VIAL

BACKGROUND

Total organic carbon (TOC) analyzers are used for, among other purposes, cleaning validation of systems containing organic carbon. Descriptions of TOC analyzers can be found in U.S. Pat. Nos. 5,132,094 and 5,902,751, both of which are fully incorporated by reference. Some TOC analyzers, such as the Sievers M9 On-Line TOC Analyzer, provide for both internetwork operating system (iOS) analysis and grab analysis. The iOS system allows for continuous measurement of the TOC level in a system by plumbing the TOC analyzer into the system. The grab analysis port of the TOC analyzer allows for a vial to be filled with a TOC sample and inserted into the grab analysis port of the TOC analyzer to perform a snap-shot analysis of the sample within the vial. However, the vial is not plumbed into the system and does not provide a continuous measurement of the TOC sample.

The iOS systems in some TOC analyzers require a minimum flow rate of the TOC sample through the iOS system for an analysis to be conducted. Furthermore, some TOC analyzers require that the minimum flow rate of the sample be maintained through the iOS system for a minimum time period.

However, some sample systems are not capable of producing a high enough flow rate of a TOC sample or maintaining flow of the TOC sample through the iOS system for the minimum required time period. Thus, a need exists for a device for analyzing continuously flowing TOC samples using a TOC analyzer at a relatively lower flow rate and for a relatively shorter period of time.

SUMMARY

Various implementations include a device for analyzing total organic carbon (TOC) within a fluid. The device includes a primary container, an input conduit, and an output conduit. The primary container is hollow and has a primary side wall and a primary end wall. The primary side wall has an inner surface defining a primary cavity and an outer surface opposite and spaced apart from the inner surface. The primary end wall includes a septum that is resiliently penetrable by an analyzer needle of a grab analysis port of a TOC analyzer. The input conduit has an input lumen. The input conduit extends through the primary container such that the input lumen is in fluid communication with the primary cavity. The output conduit has an output lumen.

In some implementations, the device includes a hollow secondary container having a secondary side wall and a secondary end wall. The secondary side wall has an inner surface and an outer surface opposite and spaced apart from the inner surface. A portion of the inner surface of the primary side wall and a portion of the inner surface of the secondary wall at least partially define a secondary cavity. The secondary end wall extends from the secondary side wall to the primary side wall. In some implementations, the output conduit extends through the secondary container such that the output lumen is in fluid communication with the secondary cavity. In some implementations, the input conduit extends through the primary container and the second container.

In some implementations, the first conduit includes a first conduit portion and a second conduit portion. The second conduit portion has a first end and a second end opposite and spaced apart from the first portion. The first end is coupled to the first portion and the second end is closer to the septum than the first end.

In some implementations, the septum comprises silicone.

In some implementations, a portion of the primary container is sized to be received within a grab analysis port of a Sievers M9 TOC analyzer.

In some implementations, a portion of the primary side wall defines threads extending from the primary end wall.

In some implementations, the input conduit and output conduit are sized to allow a flow rate through the device ranging from 0.5 mL/min to 50 mL/min.

In some implementations the device comprises polyethylene.

Various other implementations include a system for analyzing total organic carbon (TOC) within a fluid. The system includes a TOC analyzer and a device for analyzing TOC within a fluid. The TOC analyzer has an iOS and a grab analysis port. The grab analysis port includes at least one analyzer needle. The device includes a primary container, an input conduit, and an output conduit. The primary container is hollow and has a primary side wall and a primary end wall. The primary side wall has an inner surface defining a primary cavity and an outer surface opposite and spaced apart from the inner surface. The primary end wall includes a septum that is resiliently penetrable by an analyzer needle of a grab analysis port of a TOC analyzer. The input conduit has an input lumen. The input conduit extends through the primary container such that the input lumen is in fluid communication with the primary cavity. The output conduit has an output lumen. A portion of the primary container of the device for analyzing TOC within a fluid is disposed within the grab analysis port of the TOC analyzer.

In some implementations, the device includes a hollow secondary container having a secondary side wall and a secondary end wall. The secondary side wall has an inner surface and an outer surface opposite and spaced apart from the inner surface. A portion of the inner surface of the primary side wall and a portion of the inner surface of the secondary wall at least partially define a secondary cavity. The secondary end wall extends from the secondary side wall to the primary side wall. In some implementations, the output conduit extends through the secondary container such that the output lumen is in fluid communication with the secondary cavity. In some implementations, the input conduit extends through the primary container and the second container.

In some implementations, the first conduit includes a first conduit portion and a second conduit portion. The second conduit portion has a first end and a second end opposite and spaced apart from the first portion. The first end is coupled to the first portion and the second end is closer to the septum than the first end.

In some implementations, the septum comprises silicone.

In some implementations, a portion of the primary container is sized to be received within a grab analysis port of a Sievers M9 TOC analyzer.

In some implementations, a portion of the primary side wall defines threads extending from the primary end wall.

In some implementations, the input conduit and output conduit are sized to allow a flow rate through the device ranging from 0.5 mL/min to 50 mL/min.

In some implementations, the device comprises polyethylene.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

The devices and methods disclosed herein provide for a single-use device for inserting into a grab analysis port of a TOC analyzer that allows for continuous measurement from a TOC sample line. The device includes a primary container that is open at one end and is partially disposed within a secondary container that is also open at one end. The primary container of the device is sized to be inserted in the grab analysis port of a TOC analyzer and includes a septum that can be penetrated by the analyzer needles of the grab analysis port. An input conduit is in fluid communication with the cavity defined by the primary container, and an output conduit is in fluid communication with the cavity defined between the secondary conduit and the primary conduit.

When the device is inserted into the grab analysis port of a TOC analyzer and a sample line is fluidly connected to the input conduit, the sample flows into the primary container and is analyzed by the analyzer needles protruding through the septum. As the primary container fills with the sample, the sample overflows the open end of the primary container, into the secondary container, and through the output conduit. Because the primary container defines a relatively small volume and the sample is being deposited directly onto the analyzer needles of the grab analysis port, a TOC sample can be analyzed at a lower flow rate and for a shorter time period than when a sample is analyzed using the iOS system.

Various implementations include a device for analyzing total organic carbon (TOC) within a fluid. The device includes a primary container, an input conduit, and an output conduit. The primary container is hollow and has a primary side wall and a primary end wall. The primary side wall has an inner surface defining a primary cavity and an outer surface opposite and spaced apart from the inner surface. The primary end wall includes a septum that is resiliently penetrable by an analyzer needle of a grab analysis port of a TOC analyzer. The input conduit has an input lumen. The input conduit extends through the primary container such that the input lumen is in fluid communication with the primary cavity. The output conduit has an output lumen.

Various other implementations include a system for analyzing total organic carbon (TOC) within a fluid. The system includes a TOC analyzer and a device for analyzing TOC within a fluid. The TOC analyzer has an iOS and a grab analysis port. The grab analysis port includes at least one analyzer needle. The device includes a primary container, an input conduit, and an output conduit. The primary container is hollow and has a primary side wall and a primary end wall. The primary side wall has an inner surface defining a primary cavity and an outer surface opposite and spaced apart from the inner surface. The primary end wall includes a septum that is resiliently penetrable by an analyzer needle of a grab analysis port of a TOC analyzer. The input conduit has an input lumen. The input conduit extends through the primary container such that the input lumen is in fluid communication with the primary cavity. The output conduit has an output lumen. A portion of the primary container of the device for analyzing TOC within a fluid is disposed within the grab analysis port of the TOC analyzer.

Figure 1:
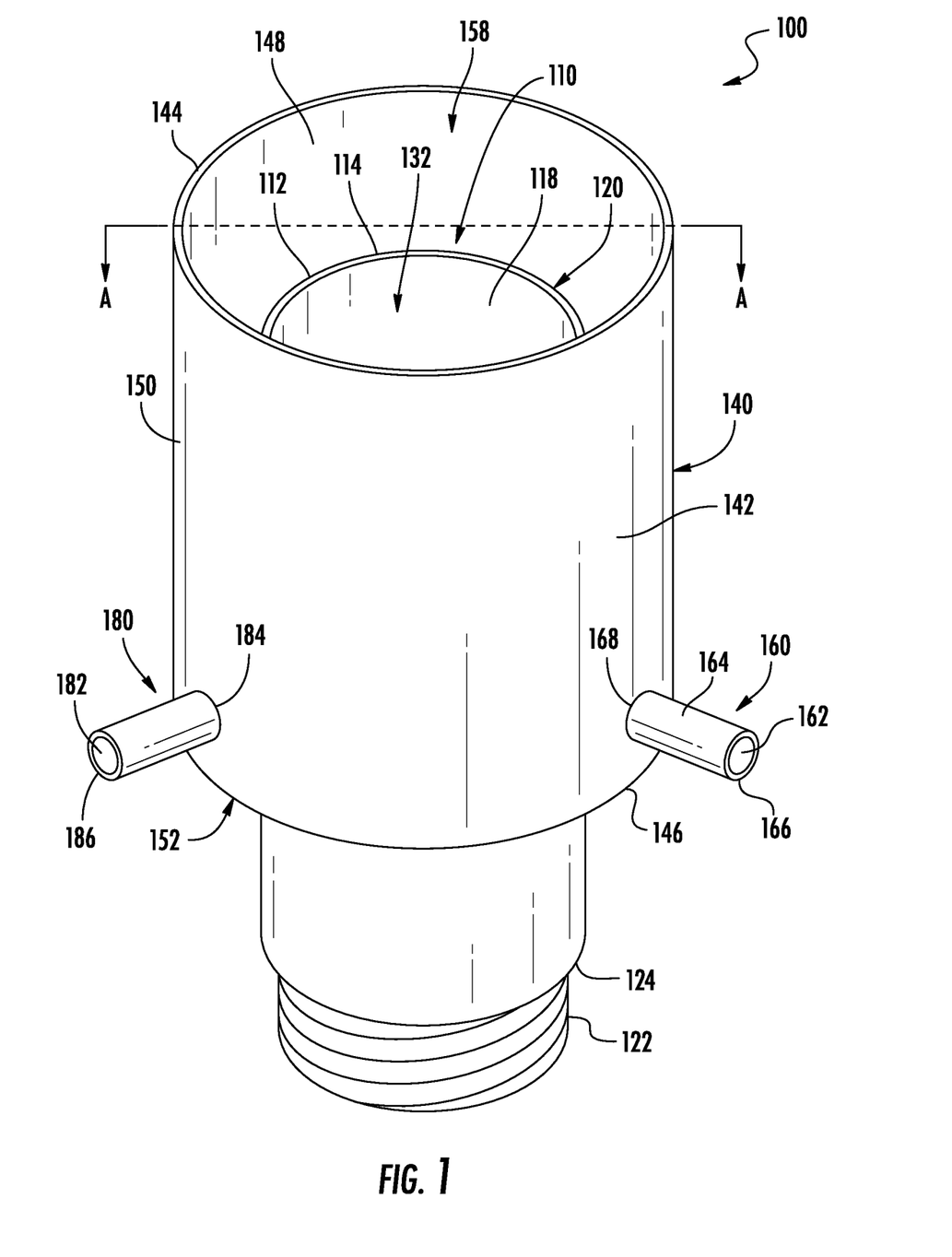
FIG. 1 shows a perspective view of a device for analyzing TOC within a fluid according to one implementation.
Figure 2:
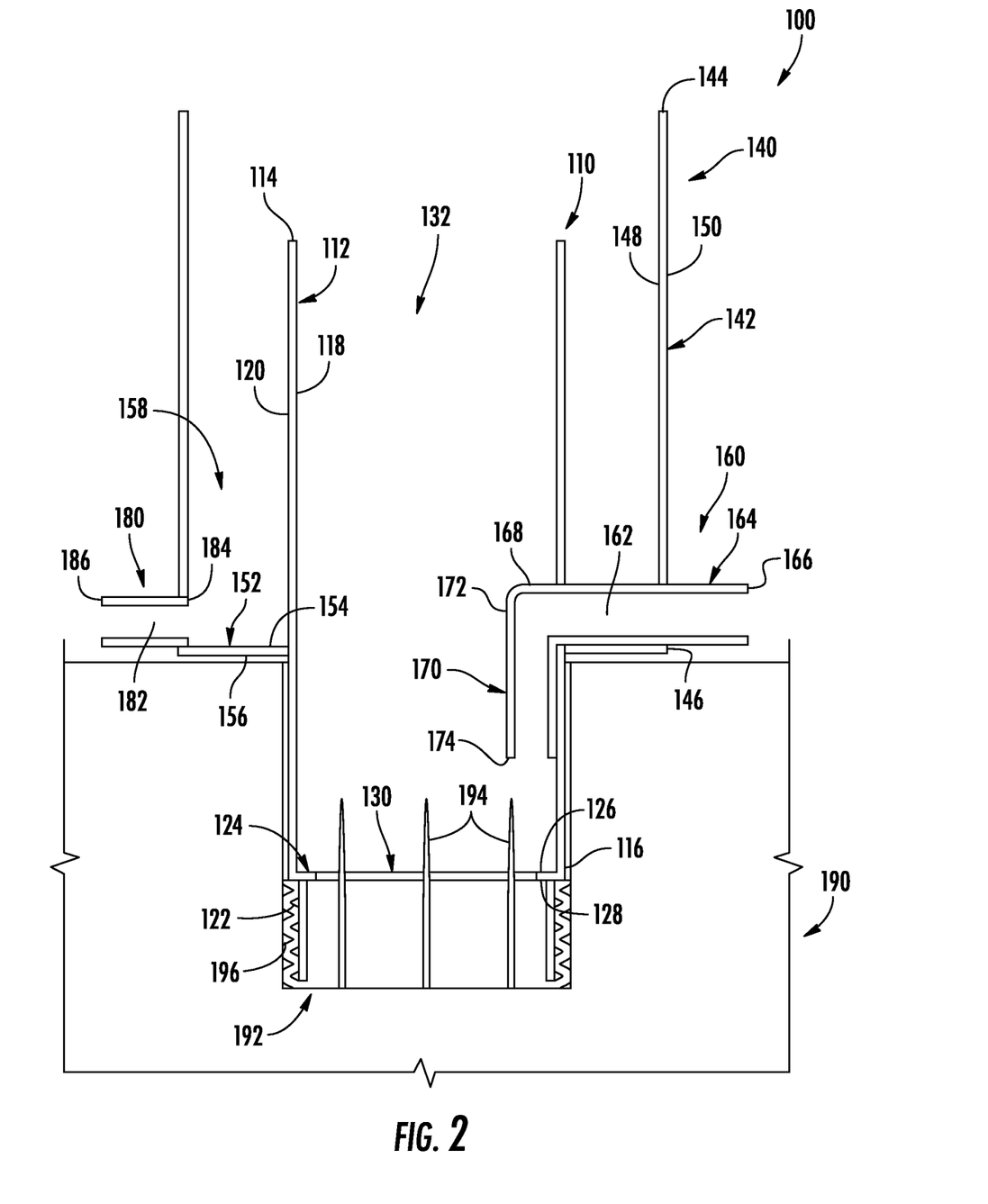
FIG. 2 shows a cross-sectional view along line A-A of the device of FIG. 1 inserted into the grab analysis port of a TOC analyzer.

FIGS. 1 and 2 show a device 100 for analyzing TOC within a fluid sample. The device 100 includes a primary container 110, a secondary container 140, an input conduit 160, and an output conduit 180. The primary container 110 is hollow and has an annular primary side wall 112 and a primary end wall 124. The primary side wall 112 has a first end 114, a second end 116 opposite and spaced apart from the first end 114, an inner surface 118, and an outer surface 120 opposite and spaced apart from the inner surface 118. The primary side wall 112 shown in FIGS. 1 and 2 has a round cross section in a plane parallel to the first end 114 of the primary side wall 112, but in other implementations, the cross section of the primary side wall is ovular, triangular, square, rectangular, pentagonal, hexagonal, or any other closed shape.

The primary end wall 124 of the primary container 110 has an inner surface 126 and an outer surface 128 spaced apart and opposite the inner surface 126. The primary end wall 124 includes a septum 130 that is resiliently penetrable by an analyzer needle 194 of a grab analysis port 192 of a TOC analyzer 190, as discussed below. The primary end wall 124 is coupled to the second end 116 of the primary side wall 112, and the inner surface 118 of the primary side wall 112 and the inner surface 126 of the primary end wall 124 define a primary cavity 132. The first end 114 of the primary container 110 is open such that the primary cavity 132 is in fluid communication with the exterior of the primary container 110. The septum 130 shown in FIGS. 1 and 2 comprises silicone, but in other implementations, the septum includes any pliable polymer or any other material capable of resiliently sealing an opening in the septum created by the penetration, and subsequent removable, of an analyzer needle.

The second end 116 of the primary container 110 shown in FIGS. 1 and 2 is sized to be received within a grab analysis port 192 of a Sievers M9 TOC analyzer. A portion of the primary side wall 112 adjacent the second end 116 defines threads 122 extending from the primary end wall 124 to engage the threads 196 of the grab analysis port 192. However, in other implementations, the second end of the primary container is sized to be received within a grab analysis port of any other make and/or model of TOC analyzer. In other implementations, the primary side wall does not include threads or includes any other fastening device configured to engage the grab analysis port of any other make and/or model of TOC analyzer.

The primary side wall 112 and primary end wall 124 of the device 100 shown in FIGS. 1 and 2 are made of High Density Polyethylene (HDPE), but in other implementations, the primary side wall and primary end wall are made of polyethylene, any other plastic, metal, glass, or any other material capable of containing a fluid TOC sample within the primary cavity.

The secondary container 140 is hollow and has an annular secondary side wall 142 and a secondary end wall 152. The secondary side wall 142 has a first end 144, a second end 146 opposite and spaced apart from the first end 144, an inner surface 148, and an outer surface 150 opposite and spaced apart from the inner surface 148. The secondary side wall 142 shown in FIGS. 1 and 2 has a round cross section in a plane parallel to the first end 144 of the secondary side wall 142, but in other implementations, the cross section of the secondary side wall is ovular, triangular, square, rectangular, pentagonal, hexagonal, or any other closed shape.

The secondary container 140 also has a secondary end wall 152 having an inner surface 154 and an outer surface 156 spaced apart and opposite the inner surface 154. The secondary end wall 152 extends between the second end 146 of the secondary side wall 142 and the outer surface 120 of the primary side wall 112. The inner surface 148 of the secondary side wall 142, the inner surface 154 of the secondary end wall 152, and the outer surface 120 of the primary side wall 112 define a secondary cavity 158.

The secondary side wall 142 and secondary end wall 152 of the device 100 shown in FIGS. 1 and 2 are made of High Density Polyethylene (HDPE), but in other implementations, the secondary side wall and secondary end wall are made of polyethylene, any other plastic, metal, glass, or any other material capable of containing a fluid TOC sample within the secondary cavity.

The input conduit 160 defines an input lumen 162 and has a first conduit portion 164 and a second conduit portion 170. The first conduit portion 164 has a first end 166 and a second end 168 spaced apart and opposite the first end 166 of the first conduit portion 164. The second conduit portion 170 has a first end 172 and a second end 174 spaced apart and opposite the first end 172 of the second conduit portion 170. The second end 168 of the first conduit portion 164 is coupled to the first end 172 of the second conduit portion 170. The input conduit 160 extends through the secondary side wall 142 and through the primary side wall 112 such that the first end 166 of the first conduit portion 164 is disposed outside of the primary cavity 132 and the secondary cavity 158 and the second end 174 of the second conduit portion 170 is disposed inside the primary cavity 132. The input lumen 162 is in fluid communication with the primary cavity 132. The second conduit portion 170 is perpendicular to the first conduit portion 164 such that the second end 174 of the second conduit portion 170 is closer to the septum 130 than both the first end 172 of the second conduit portion 170 and the second end 168 of the first conduit portion 164. However, in other implementations, the second conduit portion is at any angle transverse to the first conduit portion such that the second end of the second conduit portion is closer to the septum than both the first end of the second conduit portion and the second end of the first conduit portion. Although the input conduit 160 shown in FIGS. 1 and 2 extends through both the primary side wall 112 and the secondary side wall 142, in some implementations, the input conduit extends through one, none, or any combination of the primary side wall, the secondary side wall, the primary end wall, or the secondary end wall such that the first end of the first conduit portion is disposed outside the primary cavity and the secondary cavity and the second end of the second conduit portion is disposed inside the primary cavity.

The output conduit 180 defines an output lumen 182 and has a first end 184 and a second end 186 opposite and spaced apart from the first end 184 of the output conduit 180. The output conduit 180 extends through the secondary side wall 142 such that the first end 184 of the output conduit 180 is disposed in the secondary cavity 158 and the second end 186 of the output conduit 180 is disposed outside of the primary cavity 132 and the secondary cavity 158. The output lumen 182 is in fluid communication with the secondary cavity 158. Although the output conduit 180 shown in FIGS. 1 and 2 extends through the secondary side wall 142, in some implementations, the output conduit extends through the secondary end wall, through both the secondary side wall and secondary end wall, or does not extend through any walls such that the first end of the output conduit is disposed inside the secondary cavity and the second end of the output conduit is disposed outside the primary cavity and the secondary cavity.

In use, the device 100 is inserted into the grab analysis port 192 of a TOC analyzer 190 such that the analyzer needles 194 of the grab analysis port 192 penetrate the septum 130 of the primary container 110 and protrude into the primary cavity 132. A TOC sample line from the fluid system to be sampled is coupled to the first end 166 of the first conduit portion 164 of the input conduit 160 and an output line is coupled to the second end 186 of the output conduit 180. The TOC sample flows through the input lumen 162 of the input conduit 160 until it exits the input conduit 160 through the second end 174 of the second conduit portion 170 of the input conduit 160. Because of the angle of the second conduit portion 170 of the input conduit 160, the TOC sample flows out of the input conduit 160 and directly onto the analyzer needles 194 protruding through the septum 130.

Once the primary cavity 132 is filled with the TOC sample, the TOC sample flows over the open first end 114 of the primary container 110 and into the secondary cavity 158. Because the first end 114 of the primary container 110 is open, any gases in the TOC sample are able to escape through the opening. The TOC sample then flows into the first end 184 of the output conduit 180, through the output lumen 182, and into the output line.

Because the volume of the primary cavity 132 is relatively small and the TOC sample flows out of the input conduit 160 directly onto the analyzer needles 194, a TOC sample can be analyzed at a lower flow rate than the minimum flow rate required for analysis using the iOS system of the TOC analyzer 190. For example, the minimum flow rate for the iOS system of the Sievers M9 On-Line TOC Analyzer is 50 mL/min. The device 100 shown in FIGS. 1 and 2 is sized to allow for analysis of a TOC sample at a flow rate as low as 0.5 mL/min. In some implementations, the device is sized to allow for analysis of a TOC sample at any flow rate from 0.5 mL/min to 50 mL/min. In some implementations, the device is sized to allow for analysis of a TOC sample at any flow rate from 0.5 mL/min to 500 mL/min. Furthermore, because the grab analysis port 192 does not require a minimum time period for a sample to be analyzed, a relatively shorter TOC analysis can be performed using the device 100.

Figure 3:
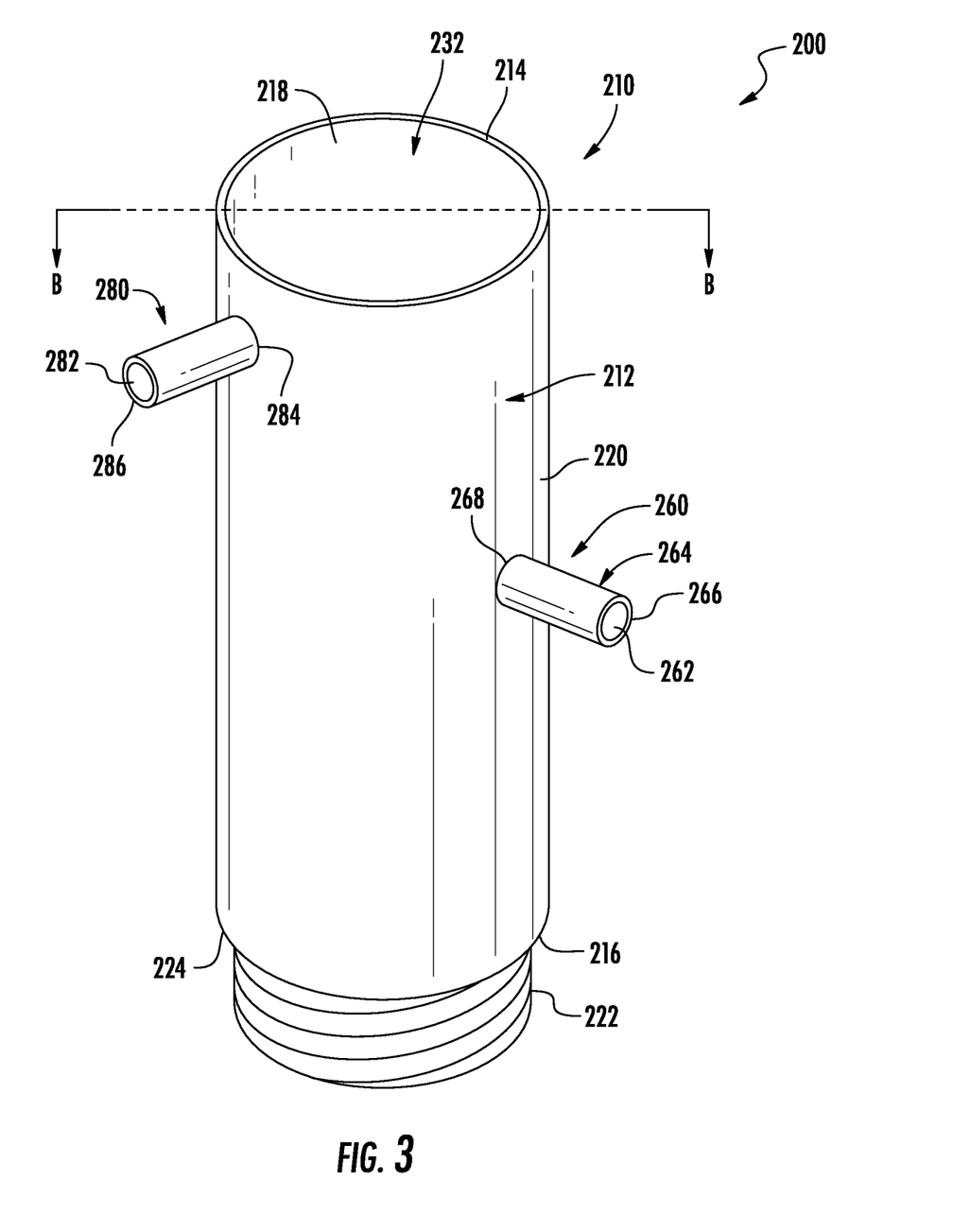
FIG. 3 shows a perspective view of a device for analyzing TOC within a fluid, according to another implementation.
Figure 4:
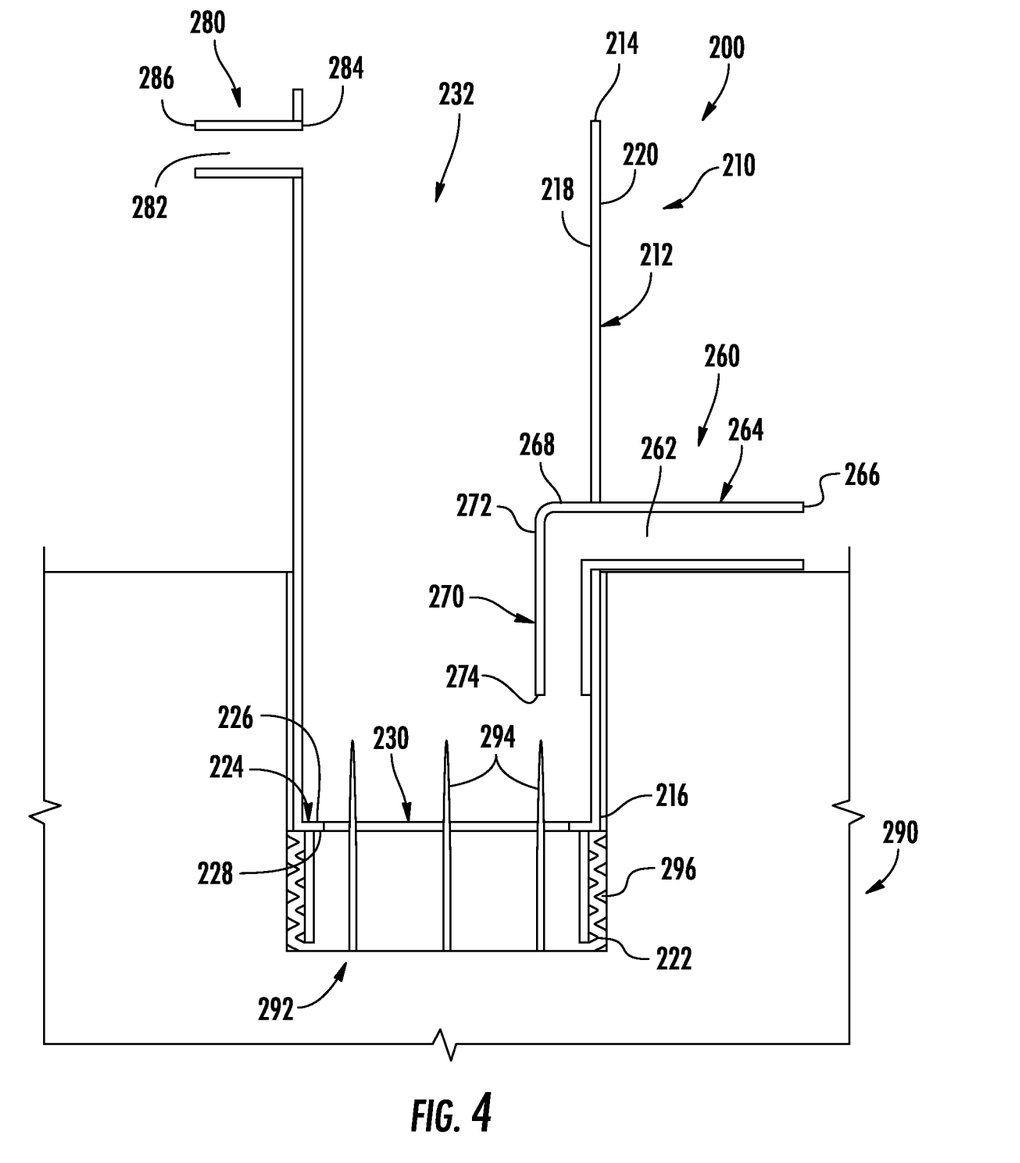
FIG. 4 shows a cross-sectional view along line B-B of the device of FIG. 3 inserted into the grab analysis port of a TOC analyzer.

FIGS. 3 and 4 show another implementation of a device 200 for analyzing TOC within a fluid sample. The device 200 includes a primary container 210, an input conduit 260, and an output conduit 280. The primary container 210 is hollow and has an annular primary side wall 212 and a primary end wall 224. The primary side wall 212 has a first end 214, a second end 216 opposite and spaced apart from the first end 214, an inner surface 218, and an outer surface 220 opposite and spaced apart from the inner surface 218. The primary side wall 212 shown in FIGS. 3 and 4 has a round cross section in a plane parallel to the first end 214 of the primary side wall 212, but in other implementations, the cross section of the primary side wall is ovular, triangular, square, rectangular, pentagonal, hexagonal, or any other closed shape.

The primary end wall 224 of the primary container 210 has an inner surface 226 and an outer surface 228 spaced apart and opposite the inner surface 226. The primary end wall 224 includes a septum 230 that is resiliently penetrable by an analyzer needle 294 of a grab analysis port 292 of a TOC analyzer 290, as discussed below. The primary end wall 224 is coupled to the second end 216 of the primary side wall 212, and the inner surface 218 of the primary side wall 212 and the inner surface 226 of the primary end wall 224 define a primary cavity 232. The first end 214 of the primary container 210 is open such that the cavity is in fluid communication with the exterior of the primary container 210. The septum 230 shown in FIGS. 3 and 4 comprises silicone, but in other implementations, the septum includes any other material capable of resiliently sealing an opening in the septum created by the penetration, and subsequent removable, of an analyzer needle.

The second end 216 of the primary container 210 shown in FIGS. 3 and 4 is sized to be received within a grab analysis port 292 of a Sievers M9 TOC analyzer. A portion of the primary side wall 212 adjacent the second end 216 defines threads 222 extending from the primary end wall 224 to engage the threads 296 of the grab analysis port 292. However, in other implementations, the second end of the primary container is sized to be received within a grab analysis port of any other make and/or model of TOC analyzer. In other implementations, the primary side wall does not include threads or includes any other fastening device configured to engage the grab analysis port of any other make and/or model of TOC analyzer.

The primary side wall 212 and primary end wall 224 of the device 200 shown in FIGS. 3 and 4 are made of High Density Polyethylene (HDPE), but in other implementations, the primary side wall and primary end wall are made of polyethylene, any other plastic, metal, glass, or any other material capable of containing a fluid TOC sample within the primary cavity.

The input conduit 260 defines an input lumen 262 and has a first conduit portion 264 and a second conduit portion 270. The first conduit portion 264 has a first end 266 and a second end 268 spaced apart and opposite the first end 266 of the first conduit portion 264. The second conduit portion 270 has a first end 272 and a second end 274 spaced apart and opposite the first end 272 of the second conduit portion 270. The second end 268 of the first conduit portion 264 is coupled to the first end 272 of the second conduit portion 270. The input conduit 260 extends through the primary side wall 212 such that the first end 266 of the first conduit portion 264 is disposed outside of the primary cavity 232 and the second end 274 of the second conduit portion 270 is disposed inside the primary cavity 232. The input lumen 262 is in fluid communication with the primary cavity 232. The second conduit portion 270 is perpendicular to the first conduit portion 264 such that the second end 274 of the second conduit portion 270 is closer to the septum 230 than both the first end 272 of the second conduit portion 270 and the second end 268 of the first conduit portion 264. However, in other implementations, the second conduit portion is at any angle transverse to the first conduit portion such that the second end of the second conduit portion is closer to the septum than both the first end of the second conduit portion and the second end of the first conduit portion. Although the input conduit 260 shown in FIGS. 3 and 4 extends through the primary side wall 212, in some implementations, the input conduit extends through one of, none of, or both of the primary side wall and the primary end wall such that the first end of the first conduit portion is disposed outside the primary cavity and the second end of the second conduit portion is disposed inside the primary cavity.

The output conduit 280 defines an output lumen 282 and has a first end 284 and a second end 286 opposite and spaced apart from the first end 284 of the output conduit 280. The output conduit 280 extends through the primary side wall 212 such that the first end 284 of the output conduit 280 is disposed in the primary cavity 232 and the second end 286 of the output conduit 280 is disposed outside of the primary cavity 232. The output lumen 282 is in fluid communication with the primary cavity 232 and is closer than the second end 274 of the second conduit portion 270 of the input conduit 260 to the first end 214 of the primary container 210. Although the output conduit 280 shown in FIGS. 3 and 4 extends through the primary side wall 212, in some implementations, the output conduit extends through one of, none of, or both of the primary side wall and the primary end wall such that the first end of the output conduit is disposed inside the primary cavity and the second end of the output conduit is disposed outside the primary cavity.

In use, the device 200 is inserted into the grab analysis port 292 of a TOC analyzer 290 such that the analyzer needles 294 of the grab analysis port 292 penetrate the septum 230 of the primary container 210 and protrude into the primary cavity 232. A TOC sample line from the fluid system to be sampled is coupled to the first end 266 of the first conduit portion 264 of the input conduit 260 and an output line is coupled to the second end 286 of the output conduit 280. The TOC sample flows through the input lumen 262 of the input conduit 260 until it exits the input conduit 260 through the second end 274 of the second conduit portion 270 of the input conduit 260. Because of the angle of the second portion of the input conduit 260, the TOC sample flows out of the input conduit 260 and directly onto the analyzer needles 294 protruding through the septum 230.

As the primary cavity 232 is filled with the TOC sample, the TOC sample reaches the first end 284 of the output conduit 280 and flows into the first end 284 of the output conduit 280, through the output lumen 282, and into the output line. Because the first end 214 of the primary container 210 is open, any gases in the TOC sample are able to escape through the opening.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A device for analyzing total organic carbon (TOC) within a fluid, the device comprising:
a hollow primary container having a primary side wall and a primary end wall, the primary side wall having an inner surface at least partially defining a primary cavity and an outer surface opposite and spaced apart from the inner surface, wherein the primary end wall includes a septum that is resiliently penetrable by an analyzer needle of a grab analysis port of a TOC analyzer;
an input conduit having an input lumen, the input conduit extending through the primary container such that the input lumen is in fluid communication with the primary cavity;
an output conduit having an output lumen; and
a hollow secondary container having a secondary side wall and a secondary end wall, the secondary side wall having an inner surface and an outer surface opposite and spaced apart from the inner surface, wherein a portion of the inner surface of the primary side wall and a portion of the inner surface of the secondary wall at least partially define a secondary cavity, wherein the secondary end wall extends from the secondary side wall to the primary side wall,
wherein the input conduit extends through the primary container and the secondary container.

2. The device of claim 1, wherein the output conduit extends through the secondary container such that the output lumen is in fluid communication with the secondary cavity.

3. The device of claim 1, wherein the input conduit comprises a first conduit portion and a second conduit portion, wherein the second conduit portion has a first end and a second end opposite and spaced apart from the first conduit portion, wherein the first end is coupled to the first conduit portion and the second end is closer to the septum than the first end.

4. The device of claim 1, wherein the septum comprises silicone.

5. The device of claim 1, wherein a portion of the primary container is sized to be received within a grab analysis port of a Sievers M9 TOC analyzer.

6. The device of claim 1, wherein a portion of the primary side wall defines threads extending from the primary end wall.

7. The device of claim 1, wherein the input conduit and output conduit are sized to allow a flow rate through the device ranging from 0.5 mL/min to 50 mL/min.

8. The device of claim 1, wherein the device comprises polyethylene.

9. A system for analyzing total organic carbon (TOC) within a fluid, the system comprising:
a TOC analyzer having an iOS and a grab analysis port, wherein the grab analysis port includes at least one analyzer needle; and
a device for analyzing TOC within a fluid, the device comprising:
a hollow primary container having a primary side wall and a primary end wall, the primary side wall having an inner surface at least partially defining a primary cavity and an outer surface opposite and spaced apart from the inner surface, wherein the primary end wall includes a septum that is resiliently penetrable by the at least one analyzer needle of the grab analysis port of a TOC analyzer,
an input conduit having an input lumen, the input conduit extending through the primary container such that the input lumen is in fluid communication with the primary cavity,
an output conduit having an output lumen, and
a hollow secondary container having a secondary side wall and a secondary end wall, the secondary side wall having an inner surface and an outer surface opposite and spaced apart from the inner surface, wherein a portion of the inner surface of the primary side wall and a portion of the inner surface of the secondary wall at least partially define a secondary cavity, wherein the secondary end wall extends from the secondary side wall to the primary side wall,
wherein the input conduit extends through the primary container and the second container, and
wherein a portion of the primary container of the device for analyzing TOC within a fluid is disposed within the grab analysis port of the TOC analyzer.

10. The system of claim 9, wherein the output conduit extends through the secondary container such that the output lumen is in fluid communication with the secondary cavity.

11. The system of claim 9, wherein the input conduit comprises a first conduit portion and a second conduit portion, wherein the second conduit portion has a first end and a second end opposite and spaced apart from the first conduit portion, wherein the first end is coupled to the first conduit portion and the second end is closer to the septum than the first end.

12. The system of claim 9, wherein the septum comprises silicone.

13. The system of claim 9, wherein a portion of the primary container is sized to be received within a grab analysis port of a Sievers M9 TOC analyzer.

14. The system of claim 9, wherein a portion of the primary side wall defines threads extending from the primary end wall.

15. The system of claim 9, wherein the input conduit and output conduit are sized to allow a flow rate through the device ranging from 0.5 mL/min to 50 mL/min.

16. The system of claim 9, wherein the device comprises polyethylene.

* * * * *